United States Patent
Conway (10) Patent No.: US 7,206,602 B1
(45) Date of Patent: Apr. 17, 2007

(54) WIRELESS TELEPHONE HAVING ANALOG OR SENSOR INPUT

(75) Inventor: Eileen Conway, La Jolla, CA (US)

(73) Assignee: Via Technologies, Inc., Taipei (TW)

( * ) Notice: Subject to any disclaimer, the term of this patent is extended or adjusted under 35 U.S.C. 154(b) by 449 days.

(21) Appl. No.: 10/254,921

(22) Filed: Sep. 24, 2002

(51) Int. Cl.
*H04B 1/38* (2006.01)

(52) U.S. Cl. .................... 455/556.1; 455/90.1

(58) Field of Classification Search ......... 455/414.1, 455/457, 404.1, 90.1, 558, 556.1, 566
See application file for complete search history.

(56) References Cited

U.S. PATENT DOCUMENTS

| | | | |
|---|---|---|---|
| 6,549,756 B1* | 4/2003 | Engstrom | 455/66.1 |
| 6,847,892 B2* | 1/2005 | Zhou et al. | 701/213 |
| 6,980,826 B2* | 12/2005 | Yamaguchi | 455/556.1 |
| 2003/0027593 A1* | 2/2003 | Howard et al. | 455/557 |
| 2003/0045311 A1* | 3/2003 | Larikka et al. | 455/466 |
| 2003/0171111 A1* | 9/2003 | Clark | 455/414.1 |
| 2003/0236100 A1* | 12/2003 | Fujieda et al. | 455/550.1 |
| 2004/0162035 A1* | 8/2004 | Petersen et al. | 455/90.1 |
| 2004/0266480 A1* | 12/2004 | Hjelt et al. | 455/558 |
| 2005/0043059 A1* | 2/2005 | Petite et al. | 455/557 |
| 2005/0208969 A1* | 9/2005 | Kwoen | 455/557 |
| 2005/0250440 A1* | 11/2005 | Zhou et al. | 455/12.1 |

\* cited by examiner

*Primary Examiner*—Edward F. Urban
*Assistant Examiner*—Blane J. Jackson
(74) *Attorney, Agent, or Firm*—Kirkpatrick & Lockhart Preston Gates Ellis LLP (57) ABSTRACT

Provided is a wireless telephone that includes means for initiating, receiving and conducting telephone calls via a wireless link to a base station. An interface means interfaces with a user and an input means inputs an analog electrical signal from any of multiple different devices. The type of device from which the analog electrical signal was input is identified and the analog electrical signal is converted into a digital signal. The digital signal is then processed, based on the identified type of device, so as to provide summary information. The summary information is then transmitted via the wireless link and/or provided to the user via the interface means.

29 Claims, 5 Drawing Sheets

WIRELESS TELEPHONE HAVING ANALOG OR SENSOR INPUT

BACKGROUND OF THE INVENTION

1. Field of the Invention

The present invention concerns a wireless telephone, such as a telephone for use in a cellular-based system, and is particularly directed to a wireless telephone that has an input for an analog signal or a sensor signal.

2. Description of the Related Art

Conventionally, various different monitoring devices have been used to measure and/or track different physical quantities. For example, outdoor thermometers measure and display ambient air temperature, ultraviolet monitors measure ultraviolet radiation levels, microwave detectors measure ambient microwave levels, medical thermometers measure body temperature, blood pressure monitors measure a patient's blood pressure, and so on. Typically, each such device must have its own user interface, which generally includes a display. In addition, if an electronic monitor is to be used, the device often will require its own processing circuitry for analyzing the monitored signal. The acquisition, maintenance and use of such different conventional monitoring devices often can be expensive and inconvenient.

If the user then wants to share any of the obtained information with a third party, some way of communicating that information to the third party must be devised. Conventionally, such communication commonly involves either traveling to the location of the third party (e.g., a physician in the case of physiological information) or telephoning the third party in order to orally communicate such information to the third party. Alternatively, some of the conventional monitoring devices permit stored information to be downloaded into another device, although even when using these devices travel to another location (i.e., where such other device is located) typically is required.

Thus, the conventional techniques for sharing monitor information usually involve traveling to the location of a third party or orally communicating the information to the third party. However, traveling often can be cumbersome and time-consuming, and orally communicating monitor information raises a significant possibility of introducing errors. In addition, both approaches often will require more time to communicate the desired information than is optimal, particularly in emergency situations. Thus, each of the conventional approaches has its own problems.

SUMMARY OF THE INVENTION

The present invention addresses these problems by providing a wireless telephone that inputs and processes an external analog electrical signal and/or a sensor or monitor signal.

Thus, in one aspect the invention is directed to a wireless telephone that includes means for initiating, receiving and conducting telephone calls via a wireless link to a base station. An interface means interfaces with a user and an input means inputs an analog electrical signal from any of multiple different devices. The type of device from which the analog electrical signal was input is identified (e.g., either by manual designation or through automatic detection) and the analog electrical signal is converted into a digital signal. In representative embodiments of the invention, the device is a sensor for monitoring a physiological parameter or an ambient environmental parameter. Preferably, the analog-to-digital conversion is performed by multiplexing (or time-sharing) an analog-to-digital converter within the wireless telephone. The digital signal is then processed, based on the identified type of device, so as to provide summary information. The particular summary information produced might be specified, either in whole or in part, by the user via the interface means or by an external source via the wireless link. The summary information is then transmitted via the wireless link and/or provided to the user via the interface means, e.g., upon the detection of a triggering criterion. In this regard, upon detection of a triggering criterion: a telephone call might be initiated automatically, the user might be prompted to make a telephone call, information might be uploaded via the wireless link, an audible alarm might be sounded, or any other action might be taken.

By identifying an analog input device, processing the input analog signal and outputting or uploading summary information in the foregoing manner, the present invention can allow a wireless telephone to be adaptably used in connection with a variety of input devices (such as sensor or monitor devices). As a result, duplication of hardware (e.g., processors) often can be avoided and the user can be provided with a flexible and convenient means for uploading analog input data to other electronic devices. In addition, in embodiments where an analog-to-digital converter is multiplexed, the functionality of the present invention often can be implemented in a wireless telephone without significant additional hardware, thereby minimizing costs. Moreover, the wireless capability of the telephone provides additional flexibility for modifying the processing performed on the input signal and/or for inputting additional information to be combined with the input signal.

In another aspect, the invention is directed to a wireless telephone that includes means for initiating, receiving and conducting telephone calls via a wireless link to a base station and an interface means that interfaces with a user. A signal is input from any of multiple different devices, with the signal representing at least one of: (i) a physiological parameter and (ii) an ambient environmental parameter. The type of the signal is identified (e.g. by manual designation or by automatic detection) and the signal is processed, based on the identified type of signal, so as to provide summary information. The summary information is then transmitted via the wireless link and/or provided to the user via the interface means (e.g., based upon detection of a triggering criterion).

By identifying a monitor signal and then inputting, processing, and uploading or outputting monitor data in the foregoing manner, the present invention can allow a wireless telephone to be adaptably used in connection with a variety of sensor or monitor devices. As a result, duplication of hardware (e.g., processors) often can be avoided and the user can be provided with a flexible and convenient means for uploading sensor data to other electronic devices. Moreover, the wireless capability of the telephone provides additional flexibility for modifying the processing performed on the input signal and/or for inputting additional information to be combined with the input signal.

The foregoing summary is intended merely to provide a brief description of the general nature of the invention. A more complete understanding of the invention can be obtained by referring to the claims and the following detailed description of the preferred embodiments in connection with the accompanying figures.

DESCRIPTION OF THE PREFERRED EMBODIMENT(S)

Figure 1:
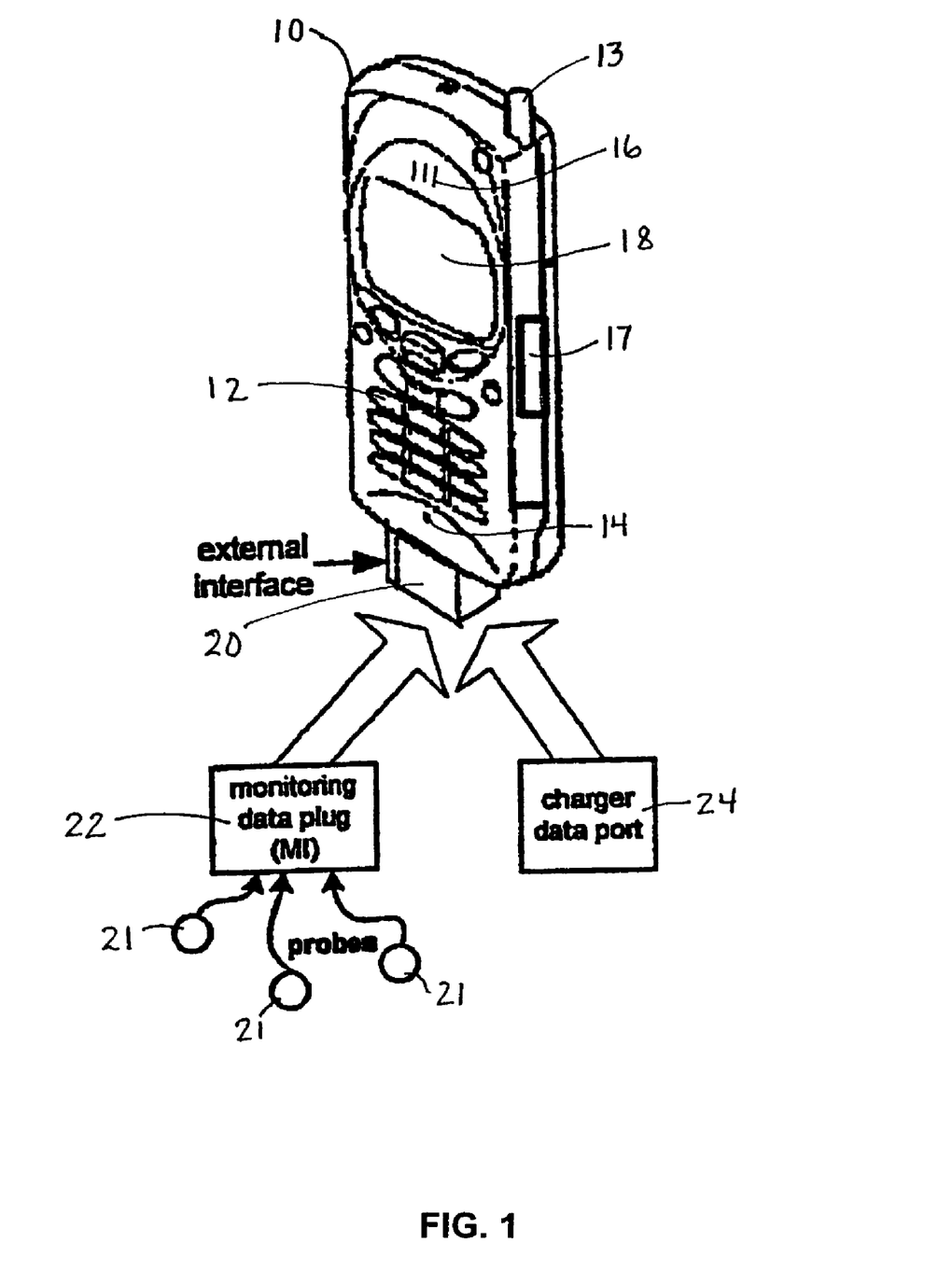
FIG. 1 is a perspective view of a wireless telephone according to a representative embodiment of the invention.

FIG. 1 illustrates a wireless telephone 10 according to the present invention, such as may be used to communicate with a fixed-position base station in a cellular-based wireless telephone system. All of the features and functionality required for initiating, receiving and conducting telephone calls are provided in wireless telephone 10. Antenna 13 allows for transmission and reception of radio frequency (RF) signals in connection with such telephone calls. In addition, telephone 10 is provided with a user interface that includes a keypad 12, a microphone 14, a speaker (or other earpiece) 16 and a liquid crystal display (LCD) 18. In operation, wireless telephone 10 may be used to place and to receive wireless telephone calls, similarly to conventional wireless telephones.

In addition to such conventional features, wireless telephone 10 is provided with an external interface 20 that includes an input port 22 for inputting digital or analog signals from a monitoring device or for inputting various other types of analog signals. Preferably, external interface 20 also includes a separate port 24 for plugging in a battery charger and for inputting other digital data. In the embodiment illustrated in FIG. 1, wireless telephone 10 is provided with inputs for multiple different monitor probes 21, each of which outputting an analog electrical signal. Wireless telephone 10 also is provided with an attached ambient temperature sensor 17.

Figure 2:
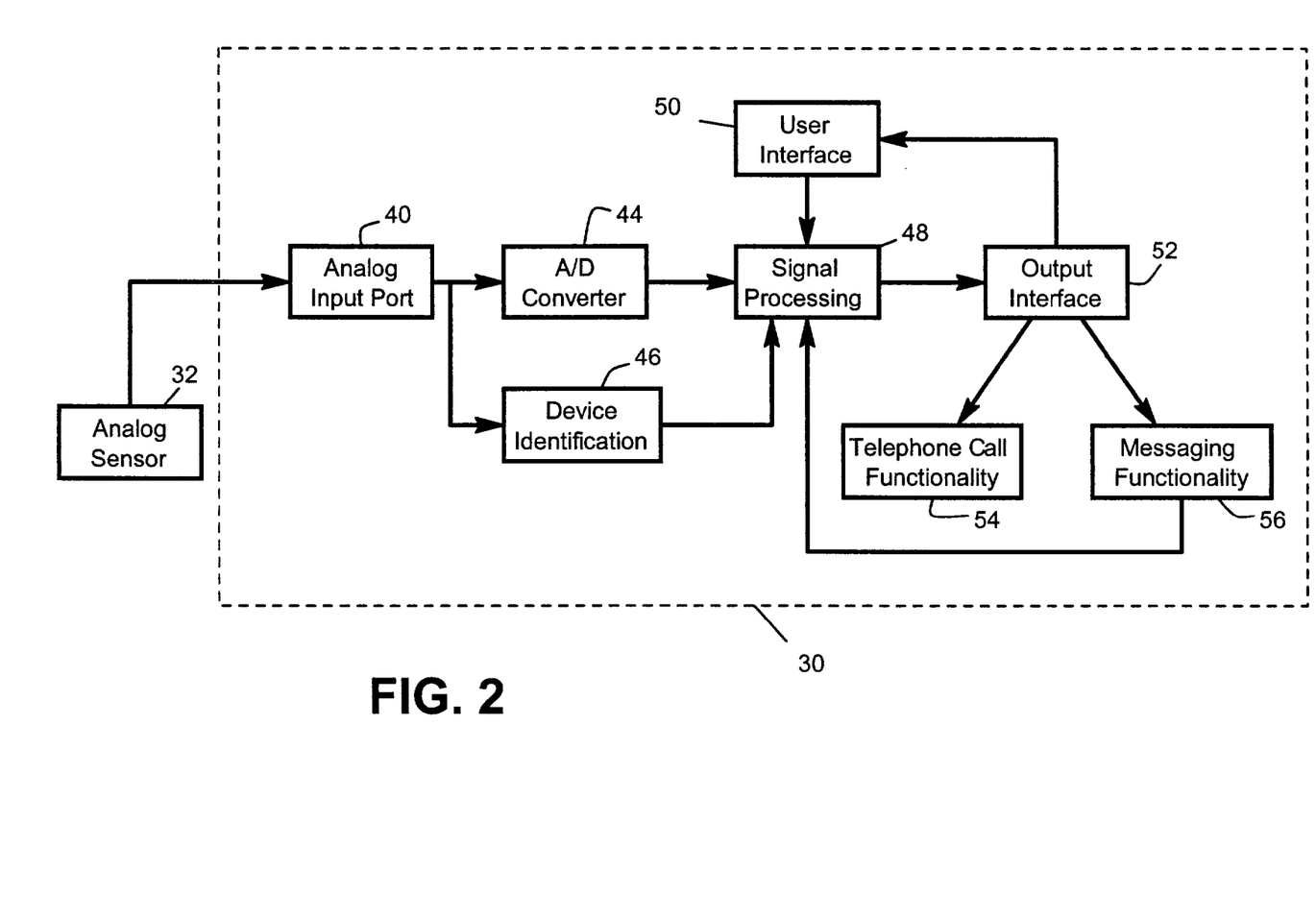
FIG. 2 is a functional block diagram of a processing system for use in a wireless telephone according to a representative embodiment of the present invention.

FIG. 2 illustrates a functional block diagram of a system 30 which may be implemented within wireless telephone 10 for processing analog input signals. The separate functional modules illustrated in FIG. 2 may be provided in hardware, software, firmware or any combination of the two. In addition, although the separation of functionality illustrated in FIG. 2 is preferred and facilitates the following discussion, any other division of functionality may instead be provided.

Provided in system 30 in the current embodiment of the invention is analog input port 40 for inputting analog signals. Preferably, analog input port 40 is a multi-pin jack. However, port 40 might instead include a female jack for accepting a standard two-conductor plug and/or might include any other standard or proprietary port. In addition, analog input port 40 may be any other type of input port for inputting analog signals via hardwired or wireless connections. With regard to the latter, analog input port 40 may include an infrared receiver or transceiver, a Bluetooth receiver or transceiver, or any other short-range radio link receiver or transceiver.

In the preferred embodiment of the invention, input port 40 inputs an analog signal from one or more analog sensing monitors 32. As used herein, a monitor or sensor means a device (e.g., an electromechanical device) that measures an actual physical parameter and outputs a corresponding electrical signal. Sensors 32 may be simple probes, such as probes 21 illustrated in FIG. 1, or may include more complicated analog circuitry. Preferably, sensors 32 monitor either physiological parameters (such as pulse, body temperature, blood pressure or heart rate) or ambient environmental parameters (such as ambient temperature or ultraviolet radiation levels). In addition, sensors 32 may or may not include their own internal power supplies. If not, power may be provided by wireless telephone 10 through analog input port 40. The signal input by port 40 is provided to analog-to-digital converter (ADC) 44 and to device identification module 46.

In ADC 44, the input analog signal input by port 40 is converted into digital format. Any known techniques for sampling and converting signals into digital format may be used by ADC 44. The resulting digital signal is then provided to signal processing module 48.

Device identification module 46 identifies the type of the device 32 that is providing the analog input signal to system 30 and outputs a (preferably digital) unique identification code therefor to signal processing module 48. In this regard, device 32 may be identified in any of a number of different ways. For instance, a set of pins in analog input port 40 may be reserved for identification purposes. In such an embodiment, the particular combination of the voltages on such pins (e.g., high or low) could be used to uniquely identify the type of device 32 or the type of signal output by device 32. A more complicated sensor 32 might output a specific analog signal on a single pin in order to uniquely the type of device or signal.

In any event, module 46 preferably permits automatic identification of the type of device 32 (or, correspondingly, the type of signal output by device 32). Thus, merely plugging in sensor 32 preferably permits system 30 to automatically determine, for example, that sensor 32 is a heart-rate monitor. Although not illustrated in FIG. 2, it should be noted that this identification information also can be provided to ADC 44, so that ADC 44 can adjust its sampling rate and/or its quantization resolution and/or its dynamic range based on the expected signal type. Although the type of device 32 (or the type of signal output by device 32) may instead be designated manually, such automatic detection is believed to minimize the chance of error, as well as to be more convenient for the user.

Also input into signal processing module 48 are commands from user interface 50. Such commands generally will indicate the user's preferences and are discussed in more detail below. User interface module 50 provides functionality for coordinating input and output signals from and to the user interface components of telephone 10 discussed above. Thus, for example, user interface 50 might display a menu-driven interface for inputting the user's preferences on LCD screen 18 and accept inputs via keypad 12. User interface 50 also arranges for the outputting (e.g., on LCD display 18) of any other messages generated by system 30.

Signal processing module 48 processes the raw input data from ADC 44 to provide summary statistics. The types of processing performed and the resulting statistics might, for example, be based on the device identification information input from module 46, the commands input from user interface 50 and, in certain embodiments, external messages (e.g., from messaging module 56). The summary statistics produced by module 48 are provided to output interface 52, which in turn controls the output of such information to any or all of: user interface 50, telephone call functionality module 54 or messaging module 56. Precisely where to output such summary statistics may be pre-programmed into signal processing module 48, based on the device identification information from module 46, based on messages from module 56, and/or specified by the user through user interface 50.

Thus, for example, certain information may be provided to display interface 50 to be displayed on the LCD display 18 for wireless telephone 10. In addition, the triggering of certain criteria might cause output interface 52 to initiate a telephone call via module 54 or to download information or transmit messages via messaging functionality module 56. The signal processing module 48 and output interface module 52 functionality are described in more detail below.

Telephone call functionality module 54 includes all of the functionality required for wireless telephone 10 to initiate, receive and conduct wireless telephone calls. Messaging functionality module 56 includes all of the functionality required for wireless telephone 10 to send and receive text and other non-audio messages to other electronic devices, such as by using email (for wireless telephones having Internet access) or by using the protocol suite commonly known as short message service (SMS).

Figure 3:
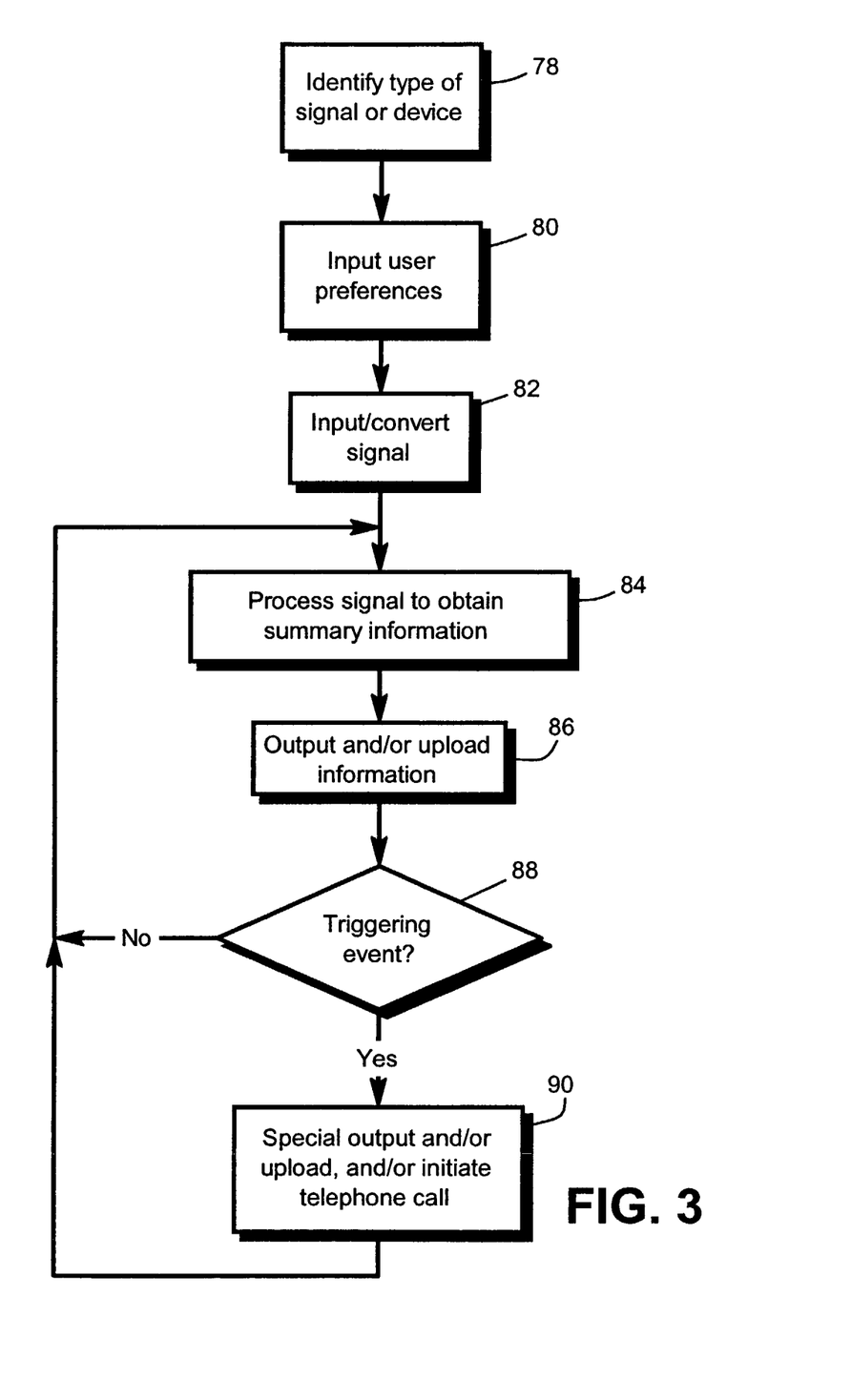
FIG. 3 is a flow diagram illustrating process steps that may be performed by the system illustrated in FIG. 2.

FIG. 3 illustrates a flow diagram for explaining the processing within a wireless telephone 10 of an analog signal provided by a monitor or sensor, according to a representative embodiment of the present invention. It should be noted that the order of the processing steps shown in FIG. 3 and discussed below is exemplary only and, in practice, the actual order of such steps may be varied significantly.

Initially, in step 78 the type of signal being input into analog input port 40 (or the type of device 32 that is connected to analog input port 40) is identified by device identification module 46. As noted above, various techniques are available for performing such identification. Alternatively, in step 78 the type of signal or type of device 32 may be designated manually via user interface 50.

In step 80, a user inputs his or her preferences for processing the input data and/or for output options via a user interface 50. Because the type of signal or device has already been identified in step 78, in step 80 the user preferably is given options that are specific to the identified signal or device. For example, if step 78 indicated that device 32 is a heart-rate monitor, then in step 80 the user might be given the options of: (i) having signal processing module 48 calculate the user's heart rate every n seconds, where n can be specified by the user through user interface 50; (ii) calculate the user's heart rate on a continuous basis; (iii) compare the user's heart rate to a desired range or threshold; and/or (iv) track changes in the user's heart rate. Generally, summary statistics regarding the input data will be generated. However, it is also possible to simply store all input data.

In addition to the types of processing to be performed, the user might be given the option of whether to store, display, or both store and display such data and/or summary statistics. The user might also be given the option of setting a threshold heart rate at which an alarm is sounded and/or a second threshold at which a message is transmitted via messaging functionality module 56 and/or a third threshold at which output interface 52 automatically causes a telephone call to be initiated via telephone call functionality module 54. Furthermore, the user might specify that the summary statistics generated in signal processing module 48 be uploaded to a third party in real time or stored and then uploaded in batch mode through messaging functionality module 56. In short, the user preferably has the ability to flexibly configure how the input data are processed and what to do with the processed data.

In certain embodiments, the user might have the ability to specify processing that compares current measurements with previous measurements or combines information from different devices 32. Still further, data provided by other sources and received by wireless telephone 10, e.g., through messaging functionality module 56, may be combined with currently input information and/or utilized to actually alter the processing of signal processing module 48. In this manner, the monitor signal processing by wireless telephone 10 can be flexibly configured based on remote sensor data or any other remote influences. The remotely provided data or instructions in this regard may be "pushed" to wireless telephone 10 by external sources (e.g., in the event of some new externally generated information) or may be "pulled" by wireless telephone 10 from external sources (e.g., where signal processing module 48 recognizes that it needs or could use such external information). For example, a newly developed and more effective processing algorithm might be pushed to wireless telephone 10 while the processing of signal processing module 48 might pull information regarding the local ambient temperature in connection with its processing of sensor data that indicate the user's body temperature.

It is noted that while the foregoing processing options are discussed as being settable by the user through user interface 50, any of such options may instead be pre-programmed to be performed by signal processing module 48 without the necessity of user input.

In step 82, an analog signal (preferably a monitor signal) is input into port 40, and then is converted into digital format in ADC 44.

In step 84, the digital signal from step 82 is processed in signal processing module 48, usually with the goal of obtaining summary information pertaining to the input data. As noted above, such processing may take different forms and usually will be dependent upon the type of signal or device identified in step 78, and often be dependent upon preferences input by the user in step 80 and/or various stored pre-defined rules. Such processing may involve calculating a number of heartbeats per minute (e.g., for heart rate monitor information), calculating a moving average, comparing generated information to specified thresholds, setting such thresholds based on other information, and/or more complicated processing such as waveform analysis (e.g., to identify an irregular heartbeat).

In step 86, the summary information calculated in step 84 is output via user interface 50 and/or uploaded (e.g., via messaging functionality module 56), as instructed by the user in step 80 or according to default rules that preferably are based upon the type of input signal or device identified in step 78. Thus, for example, if device 32 is a thermometer then a temperature might be uploaded via module 56 or displayed via user interface 50 periodically, e.g., every 60 seconds.

In step 88, a determination is made as to whether one or more triggering events have occurred. Thus, for example, a determination might be made as to whether a measured temperature has fallen below a specified minimum, risen above a specified maximum, or fallen in or out of a specified range. If not, then processing returns to step 84 to continue processing the input signal and outputting or uploading the resulting information in the usual course.

On the other hand, if a defined triggering event has in fact occurred, then in step 90 the specified action that is associated with such event is performed. Such actions might include any or all of the following: an additional output to display 18, sounding of an alert signal (e.g., using the ringer functionality of wireless telephone 10), sounding of an alert message (e.g., using the speaker 16 of wireless telephone 10), transmission of a message or other data to a third party via messaging functionality module 56, initiation of a telephone call via module 54, sounding of an alarm via user interface 50, or outputting a message via user interface 50 that suggests making a telephone call. In the latter case, the user might be prompted to make a particular telephone call using an alert signal and either a text message displayed on LCD display 18 or a voice message over speaker 16, with such message preferably allowing the user to initiate a specific call in an abbreviated manner (e.g., by pressing an "OK" button on keypad 12, a pre-programmed telephone number is dialed automatically). Thus, while step 86 provides for output of monitor data in the usual course, the combination of steps 88 and 90 allows for additional output options under specified (e.g., unusual or emergency) circumstances. In the case of transmitting a message, preferably other information also is transmitted.

Figure 4:
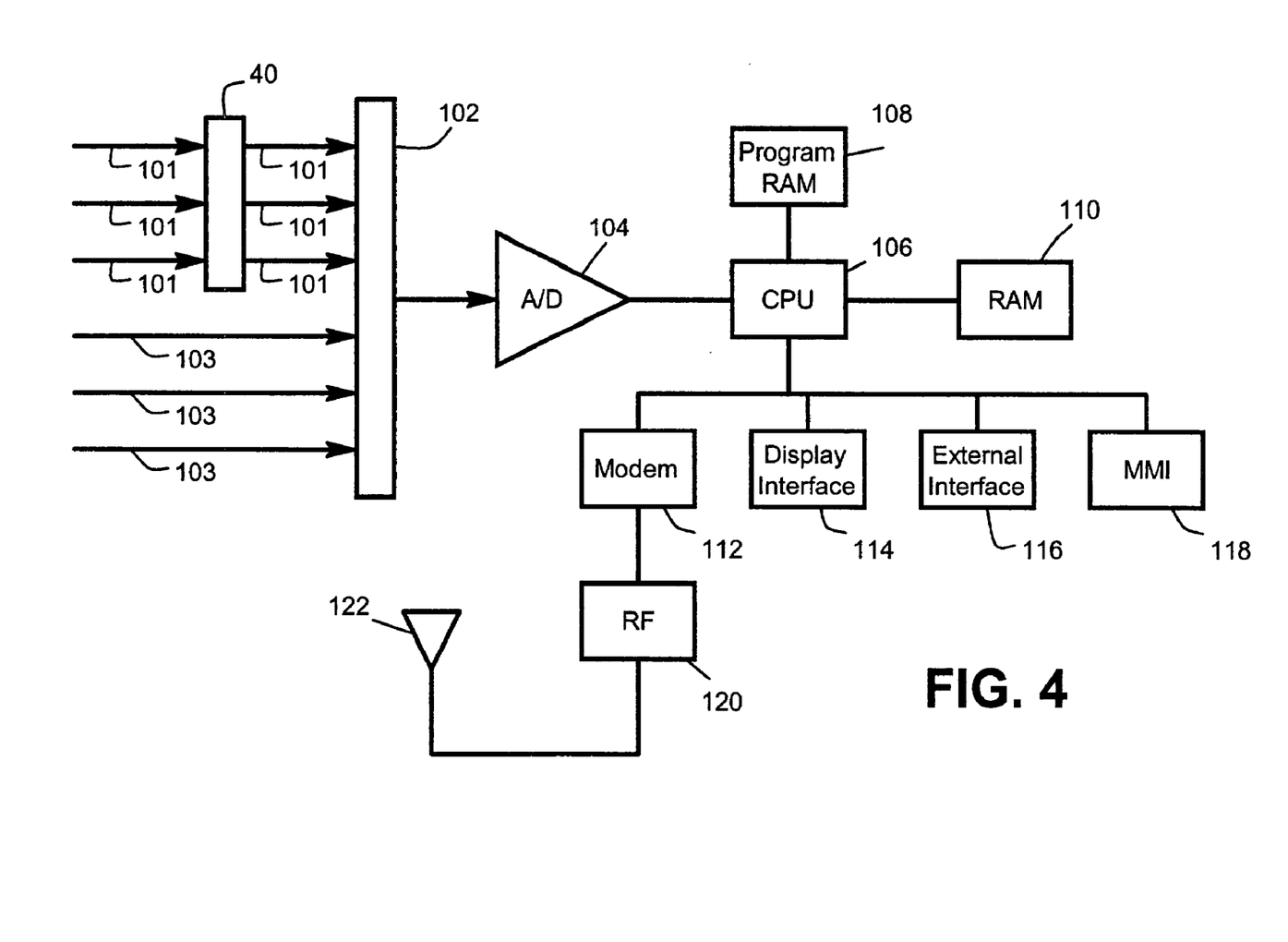
FIG. 4 is a block diagram of a wireless telephone circuit which may be used for implementing the techniques of the present invention.

FIG. 4 illustrates a circuit 100 that may be used to implement the functionality described above. Included in circuit 100 is a physical input port 40, as described above, for inputting various analog input signals 101. In the preferred embodiment of the invention, such input signals 101 are monitor signals provided by various monitoring devices. The signals 101 input into port 40 are provided into multiplexer 102. Also provided to multiplexer 102 are certain other analog signals 103 which are generated internally to wireless telephone 10. Analog signals 103 might included, for example, signals indicating any or all of temperature within wireless telephone 10 or battery voltage.

Multiplexer 102 selectively applies one of the input signals 101 or 103 at any given time to ADC 104. The precise sequence in which such signals 101 and 103 are provided to ADC 104 preferably depends upon the desired sampling rate for each such signal, which in turn will depend upon a correct identification (in step 78) of the signal type for each such input signal. By using multiplexer 102 in this way, a single ADC 104 may be utilized for a variety of input analog signals.

In ADC 104, the input analog signal is converted into a digital signal. Thus, ADC 104 performs the functionality of converter 44 shown in FIG. 2. ADC 104 may be implemented using any known technique.

Central processing unit 106 performs most of the main processing described above by executing stored program steps out of program random access memory 108 and by retrieving data from and storing data to random access memory 110.

Central processing unit 106 also interfaces with modem 112 which permits digital signals to be transmitted wirelessly via RF unit 120 and antenna 122. Display interface 114 controls the text and images displayed on display 18. External interface 116 interfaces with data port 24 thereby permitting communications between wireless telephone 10 and other digital devices. Man-machine interface 118 provides additional processing for enhancing and simplifying the user interface for wireless telephone 10. It is noted that the functionality of hardware interfaces 114 and 118 is encompassed within functional block 50 (shown in FIG. 2).

Figure 5:
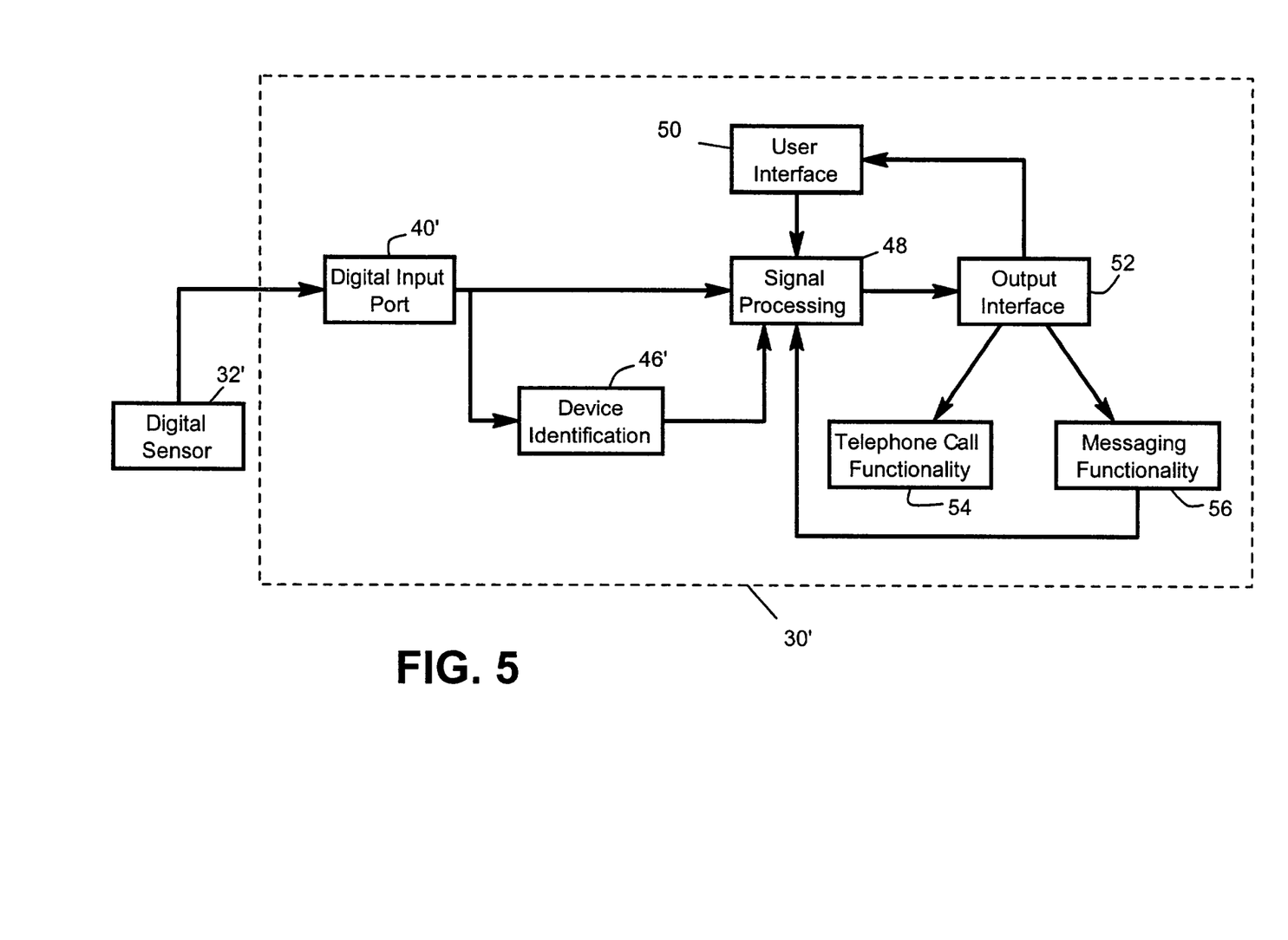
FIG. 5 is a functional block diagram of a wireless telephone processing system for inputting digital sensor data according to representative embodiment of the present invention.

FIG. 5 is a block diagram illustrating the functionality of a system 30' for implementation in wireless telephone 10 according to an embodiment of the present invention in which sensor data are input in digital format. Thus, a digital sensor 32' provides a digital signal to a digital input port 40'. For example, port 40' might include a standard universal serial bus (USB) port, an RS232 port, and/or any other standard or proprietary port. The digital signal input by port 40' is provided directly to signal processing module 48 without the need for analog-to-digital conversion.

Device identification module 46' monitors the input digital signal to identify the type of device or type of signal that is being input into wireless telephone 10. In this regard, sensor 32' might periodically insert a code indicating the type of signal or type of device. In such a case, device identification module 46' merely extracts the code and passes it on to signal processing module 48). The other functional modules of system 30' are identical to the correspondingly numbered modules described above for system 30.

System Environment

Many of the methods and techniques described herein can be practiced with a wireless telephone, any other (preferably portable) wireless device, or any other device that incorporates a general-purpose computing system. Such a computing system typically will include, for example, at least some of the following components: one or more central processing units (CPUs), read-only memory (ROM), random access memory (RAM), input/output circuitry for interfacing with other devices and for connecting to one or more networks (which in turn may connect to the Internet or to any other networks), a display (such as a liquid crystal display), other output devices (such as a speaker), one or more input devices (such as a stylus, keypad and/or microphone), and a real-time clock. In addition, a device for implementing the techniques of the present invention may include interfaces for connecting to various peripheral devices, such as a larger keyboard, a mass storage unit (e.g., a hard disk drive), a device for reading/writing to a portable storage medium (such as a magnetic diskette, a magnetic tape, an opto-magnetic disk, an optical disk, or the like), and/or a modem (which also may connect to the Internet or to any other computer network via a dial-up connection). In operation, the process steps to implement the above methods typically are initially stored in RAM or ROM and then executed by the CPU directly out of RAM or ROM.

Suitable devices for use in implementing the present invention may be obtained from various vendors. Various types of devices may be used depending upon the size and complexity of the tasks to be performed. Suitable devices include PDAs, wireless telephones or any other wireless or hard-wired networked appliance or device. In addition, the techniques of the present invention may be implemented on mainframe computers, multiprocessor computers, workstations or personal computers. Also, although a general-purpose computing system has been described above, special-purpose hardware may also (or instead) be used. In particular, any of the functionality described above can be implemented in software, hardware, firmware or any combination of these, with the particular implementation being selected based on known engineering tradeoffs.

It should be understood that the present invention also relates to machine-readable media on which are stored program instructions for performing the methods of this invention. Such media include, by way of example, magnetic disks, magnetic tape, optically readable media such as CD ROMs and DVD ROMs, semiconductor memory such as PCMCIA cards, etc. In each case, the medium may take the form of a portable item such as a small disk, diskette, cassette, etc., or it may take the form of a relatively larger or immobile item such as a hard disk drive, ROM or RAM provided in a computer or other computing device.

Additional Considerations

In the above-described embodiments of the invention, existing resources (e.g., circuitry) in a wireless telephone can be utilized to process and/or analyze signals input from an external monitor or sensor and/or other types analog signals, thereby avoiding duplication of hardware in many instances. However, in other embodiments of the invention, various other types of devices may instead be used. For example, a wireless personal digital assistant (PDA) or other small portable wireless device may instead be used.

Other variations on the above-described embodiments also are possible. For example, a device according to the present invention might be programmed to store the processed data in memory and then to upload it during off-peak times when connection costs are lower, or otherwise to incorporate transmission cost information into the decision as to when to upload information. Similarly, data might be uploaded when a specified memory capacity has been exceeded.

As noted above, in certain circumstances (e.g., in emergencies) a wireless telephone according to the present invention might automatically initiate a telephone call or message and/or automatically prompt the user to make a telephone call or send a message. In addition, such a wireless telephone might automatically transmit additional information in connection with such a telephone call or message, such as the location of the wireless telephone (which can be determined, for example, using known algorithms executed by one or more base stations and/or the wireless telephone itself).

Still further, as noted above a Bluetooth or other short-range radio link might be used to input sensor data into a device according to the present invention. If provided, such a transceiver might also (or instead) be used to download data from the device to another device, instead of using the cellular-based wireless link.

Thus, although the present invention has been described in detail with regard to the exemplary embodiments thereof and accompanying drawings, it should be apparent to those skilled in the art that various adaptations and modifications of the present invention may be accomplished without departing from the spirit and the scope of the invention. Accordingly, the invention is not limited to the precise embodiments shown in the drawings and described above. Rather, it is intended that all such variations not departing from the spirit of the invention be considered as within the scope thereof as limited solely by the claims appended hereto.

Also, several different embodiments of the present invention are described above, with each such embodiment described as including certain features. However, it is intended that the features described in connection with the discussion of any single embodiment are not limited to that embodiment but may be included and/or arranged in various combinations in any of the other embodiments as well, as will be understood by those skilled in the art.

What is claimed is:

1. A wireless telephone for initiating, receiving and conducting telephone calls via a wireless link to a base station, comprising:

a user interface for interfacing with a user;

at least one sensor for inputting an analog electrical signal indicative of one or more parameters of a surrounding thereof;

at least one device identification module for identifying a type of the sensor from which the analog electrical signal was input;

at least one analog-to-digital converter for converting the analog electrical signal into a digital signal;

at least one signal processing module for processing the digital signal based on the type of the sensor identified by the device identification module, so as to provide summary information; and at least one output interface for at least one of: (i) transmitting the summary information via the wireless link and (ii) providing the summary information to the user via the user interface, wherein the analog electrical signal is converted by time-sharing the analog-to-digital converter within the wireless telephone.

2. A wireless telephone according to claim 1, wherein the output interface transmits the summary information upon detection of a triggering criterion by the signal processing module.

3. A wireless telephone according to claim 1, wherein the type of sensor is identified by the device identification module without user input.

4. A wireless telephone according to claim 1, wherein the type of sensor monitors at least one of: (i) a physiological parameter and (ii) an ambient environmental parameter.

5. A wireless telephone according to claim 1, wherein the output interface causes a telephone call to be initiated upon detection of a triggering criterion by the signal processing module.

6. A wireless telephone according to claim 1, further comprising a messaging functionality module for, upon detection of a triggering criterion by the signal processing module, prompting the user to make a telephone call.

7. A wireless telephone according to claim 1, further comprising a hardware input jack.

8. A wireless telephone according to claim 1, further comprising a second wireless link.

9. A wireless telephone according to claim 1, wherein the user interface comprises a keypad for allowing the user to specify conditions for uploading the summary information via the wireless link and conditions for providing the summary information to the user via the user interface.

10. A wireless telephone according to claim 1, wherein the user interface comprises a keypad for allowing the user to specify a type of the summary information to be provided by the signal processing module.

11. A wireless telephone for initiating, receiving and conducting telephone calls via a wireless link to a base station, comprising:

a user interface for interfacing with a user;

at least one sensor for inputting a signal representing at least one of: (i) a physiological parameter and (ii) an ambient environmental parameter;

at least one device identification module for identifying a type of the signal;

at least one signal processing module for processing the signal based on the type of the signal identified by the device identification module, so as to provide summary information; and at least one output interface for providing the summary information to the user via the user interface, wherein the user interface comprises a liquid crystal display showing the summary information containing statistics data with regard to the parameters represented by the signal.

12. A wireless telephone according to claim 11, wherein the output interface transmits the summary information upon detection of a triggering criterion by the signal processing module.

13. A wireless telephone according to claim 11, wherein the type of signal is identified by the device identification module without user input.

14. A wireless telephone according to claim 11, wherein the output interface causes a telephone call to be initiated upon detection of a triggering criterion by the signal processing module.

15. A wireless telephone according to claim 11, further comprising a messaging functionality module for, upon detection of a triggering criterion by the signal processing module, prompting the user to make a telephone call.

16. A wireless telephone according to claim 11, further comprising a hardware input jack.

17. A wireless telephone according to claim 11, further comprising a second wireless link.

18. A wireless telephone according to claim 11, wherein the user interface comprises a keypad for allowing the user to specify conditions for uploading the summary information via the wireless link and conditions for providing the summary information to the user via the user interface.

19. A wireless telephone according to claim 11, wherein the user interface comprises a keypad for allowing the user to specify a type of the summary information to be provided by the signal processing module.

20. A method for a wireless telephone to initiate, receive and conduct telephone calls via a wireless link to a base station, comprising:

interfacing with a user via a user interface;

inputting an analog electrical signal indicative of one or more parameters of a surrounding thereof, using at least one sensor;

identifying a type of the sensor from which the analog electrical signal was input, using at least one device identification module;

converting the analog electrical signal into a digital signal, using at least one analog-to-digital converter;

processing the digital signal based on the type of the sensor identified by the device identification module using at least one signal processing module, so as to provide summary information; and transmitting the summary information via the wireless link or providing the summary information to the user via the user interface, using at least one output interface, wherein the analog electrical signal is converted by time-sharing the analog-to-digital converter within the wireless telephone.

21. The method of claim 20, wherein the output interface transmits the summary information upon detection of a triggering criterion by the signal processing module.

22. The method of claim 21, wherein the type of sensor is identified by the device identification module without user input.

23. The method of claim 20, wherein the type of sensor monitors at least one of: (i) a physiological parameter and (ii) an ambient environmental parameter.

24. The method of claim 20, wherein the output interface causes a telephone call to be initiated upon detection of a triggering criterion by the signal processing module.

25. The method of claim 20, further comprising prompting the user to make a telephone call upon detection of a triggering criterion by the signal processing module, using a messaging functionality module.

26. The method of claim 20, wherein the wireless telephone further comprises a hardware input jack.

27. The method of claim 20, wherein the wireless telephone further comprises a second wireless link.

28. The method of claim 20, wherein the user interface comprises a keypad for allowing the user to specify conditions for uploading the summary information via the wireless link and conditions for providing the summary information to the user via the user interface.

29. The method of claim 20, wherein the user interface comprises a keypad for allowing the user to specify a type of the summary information to be provided by the signal processing module.

* * * * *

UNITED STATES PATENT AND TRADEMARK OFFICE
CERTIFICATE OF CORRECTION

PATENT NO. : 7,206,602 B1  
APPLICATION NO. : 10/254921  
DATED : April 17, 2007  
INVENTOR(S) : Eileen Conway Page 1 of 1

It is certified that error appears in the above-identified patent and that said Letters Patent is hereby corrected as shown below:

On the face of Patent No.: US 7,206,602 B1, Section (73) "Assignee" should be corrected from "Via Technologies, Inc. Taipei (TW)" to "VIA Telecom Co., Ltd. San Diego (California US)"

Signed and Sealed this

Thirteenth Day of January, 2009

JON W. DUDAS  
*Director of the United States Patent and Trademark Office*